(12) United States Patent
Eidenschink

(10) Patent No.: US 7,597,702 B2
(45) Date of Patent: Oct. 6, 2009

(54) BALLOON ASSEMBLY WITH A TORQUE

(75) Inventor: Tracee Eidenschink, Wayzata, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1104 days.

(21) Appl. No.: 10/663,641

(22) Filed: Sep. 17, 2003

(65) Prior Publication Data

US 2005/0059989 A1 Mar. 17, 2005

(51) Int. Cl.
*A61M 29/00* (2006.01)
(52) U.S. Cl. ..................................... 606/194
(58) Field of Classification Search ............ 604/103.13, 604/103.14, 96.01, 99.04, 104, 105, 106, 604/107, 108, 109, 95.04; 606/191–194
See application file for complete search history.

(56) References Cited

U.S. PATENT DOCUMENTS

| | | | |
|---|---|---|---|
| 4,261,339 A | 4/1981 | Hanson et al. ................. 128/1 |
| 4,346,698 A * | 8/1982 | Hanson et al. ................. 600/18 |
| 4,362,150 A * | 12/1982 | Lombardi et al. ............. 600/18 |
| 4,422,447 A | 12/1983 | Schiff ............................. 128/1 |
| 4,467,790 A | 8/1984 | Schiff ............................. 128/1 |
| 4,483,340 A | 11/1984 | Fogarty ....................... 128/344 |
| 4,490,421 A | 12/1984 | Levy ........................... 428/35 |
| 4,697,573 A | 10/1987 | Schiff ............................. 128/1 |
| RE32,983 E | 7/1989 | Levy ........................ 428/36.92 |
| 4,906,244 A | 3/1990 | Pinchuk et al. ............. 606/194 |
| 4,941,877 A | 7/1990 | Montano, Jr. ................. 604/96 |
| RE33,561 E | 3/1991 | Levy ........................ 428/36.92 |
| 5,015,230 A | 5/1991 | Martin et al. .................. 604/96 |
| 5,147,302 A | 9/1992 | Euteneuer et al. ........... 604/103 |
| 5,226,887 A | 7/1993 | Farr et al. ...................... 604/96 |
| 5,250,069 A | 10/1993 | Nobuyoshi et al. .......... 606/192 |
| 5,330,428 A | 7/1994 | Wang et al. .................... 604/96 |
| 5,342,307 A | 8/1994 | Euteneuer et al. ........... 604/103 |
| 5,348,538 A | 9/1994 | Wang et al. .................... 604/96 |
| 5,350,361 A | 9/1994 | Tsukashima et al. .......... 604/96 |
| 5,403,340 A | 4/1995 | Wang et al. .................. 606/194 |
| 5,447,497 A | 9/1995 | Sogard et al. ................ 604/101 |
| 5,456,666 A | 10/1995 | Campbell et al. .............. 604/96 |
| 5,458,572 A | 10/1995 | Campbell et al. .............. 604/96 |
| 5,478,319 A | 12/1995 | Campbell et al. .............. 604/96 |
| 5,500,181 A | 3/1996 | Wang et al. .................. 264/532 |
| 5,556,383 A | 9/1996 | Wang et al. .................... 604/96 |
| 5,593,419 A | 1/1997 | Segar .......................... 606/196 |
| 5,681,522 A | 10/1997 | Roychowdhury ........... 264/532 |
| 5,830,182 A | 11/1998 | Wang et al. .................... 604/96 |
| 5,833,657 A | 11/1998 | Reinhardt et al. .............. 604/96 |
| 5,853,389 A | 12/1998 | Hijlkema ....................... 604/96 |
| 5,951,941 A | 9/1999 | Wang et al. .................. 264/523 |

(Continued)

FOREIGN PATENT DOCUMENTS

DE 19833501 C1 1/2000
EP 1256357 A2 11/2002

*Primary Examiner*—Kevin C Sirmons
*Assistant Examiner*—Catherine N Witczak
(74) *Attorney, Agent, or Firm*—Vidas, Arrett & Steinkraus, P.A.

(57) ABSTRACT

An expandable medical balloon for use in combination with a catheter assembly, the balloon having a torque in a first and second unexpanded state, and to methods of making and using the same.

34 Claims, 2 Drawing Sheets

U.S. PATENT DOCUMENTS

| | | |
|---|---|---|
| 5,954,740 A | 9/1999 | Ravenscroft et al. ......... 604/194 |
| 6,013,055 A | 1/2000 | Bampos et al. ................ 604/96 |
| 6,013,092 A | 1/2000 | Dehdashtian et al. ........ 604/194 |
| 6,033,380 A | 3/2000 | Butaric et al. ................. 604/96 |
| 6,071,285 A | 6/2000 | Lashinski et al. ............ 606/108 |
| 6,086,556 A | 7/2000 | Hamilton et al. ............... 604/96 |
| 6,106,530 A | 8/2000 | Harada ....................... 606/108 |
| 6,110,192 A | 8/2000 | Ravenscroft et al. ......... 606/194 |
| 6,124,007 A | 9/2000 | Wang et al. ................. 428/35.2 |
| 6,146,356 A | 11/2000 | Wang et al. .................... 604/96 |
| 6,171,278 B1 | 1/2001 | Wang et al. .................... 604/96 |
| 6,283,743 B1 | 9/2001 | Traxler et al. ................ 425/391 |
| 6,284,333 B1 | 9/2001 | Wang et al. ................. 428/35.5 |
| 6,296,655 B1 | 10/2001 | Gaudoin et al. ............. 606/194 |
| 6,406,457 B1 | 6/2002 | Wang et al. ............... 606/96.01 |
| 6,428,568 B2 | 8/2002 | Gaudoin et al. ............. 623/1.11 |
| 6,432,080 B2 | 8/2002 | Pederson, Jr. et al. .. 604/103.07 |
| 6,443,926 B1 * | 9/2002 | Kletschka ................ 604/96.01 |
| 6,468,243 B1 | 10/2002 | Miyagawa et al. ....... 604/96.01 |
| 6,544,224 B1 | 4/2003 | Steese-Bradley ....... 604/103.06 |
| 2001/0037140 A1 | 11/2001 | Gaudoin et al. ............. 623/1.11 |
| 2002/0120233 A1 | 8/2002 | Eidenschink et al. ..... 604/96.01 |
| 2003/0083687 A1 | 5/2003 | Pallazza ..................... 606/191 |

* cited by examiner

BALLOON ASSEMBLY WITH A TORQUE

BACKGROUND OF THE INVENTION

This invention relates generally to the manufacture of balloon catheters having inflatable expander members or balloon members, and to the balloon catheters made thereby.

Balloon catheters are well known and used regularly for coronary angioplasty procedures and other similar procedures. In an angioplasty procedure, an occluded blood vessel, i.e., one containing a stenosis, is treated by the inflation of a balloon member which expands the vessel lumen thus pressing the stenotic lesion back against the vessel wall. Such stenosis are often the result of atheromatous plaque adhering to a blood vessel wall and restricting blood flow therethrough which is compressed against the vessel wall by the balloon balloon member which is positioned in the vessel at the plaque location and then expanded. This dilates the vessel lumen to permit increased blood flow.

Typically, the expander member or balloon is carried on the distal end of a dilatation catheter assembly which is routed through a guide catheter that has been previously advanced through the vascular system to a location that is proximal to, for example, the coronary artery having the stenotic lesion. Following placement of the balloon member across the lesion as desired, fluid is introduced into the proximal end of the catheter to inflate the balloon member to a relatively high pressure, thereby restoring patency to the vessel.

A typical balloon catheter includes two lengthwise lumens or channels, one for inflation of an inflatable balloon tacked to the distal catheter end and the other for insertion of a guidewire extending through the catheter to aid in positioning the catheter during use.

Prior to its inflation while treating a stenotic lesion, the balloon or expander member is tightly wrapped or folded so as to exhibit a low profile at the distal end of the angioplasty catheter. This facilitates its ability to be routed through the lumen of a guide catheter and into a coronary artery for placement adjacent the lesion to be treated. Once the balloon has been inflated by injecting an inflation fluid through the inflation lumen and out the inflation port, the inflation fluid is evacuated. However, commonly employed balloon materials do not evacuate as desired, "winging" or "pancaking" upon evacuation of the inflation fluid may occur as described in U.S. Pat. No. 5,681,522. That is to say, evacuation of the inflation fluid does not result in the balloon member again tightly re-wrapping and conforming to the periphery of the catheter body. This makes it difficult to withdraw the distal end portion of the catheter back into the lumen of the guide catheter with which it is used or to perform additional manipulation of the balloon catheter within the vasculature. Thus, such balloons are said to lack sufficient rewrap such that they can be removed easily after deflation.

U.S. Pat. No. 5,853,389, there is disclosed a large balloon for a balloon catheter having a tubular central section and, when inflated, frustoconical transition sections on either end of the central section connecting with tubular end sections of less diameter than the central section. The transition sections have spiral ridges of material extending from each end section toward the central section, and in which, in deflated condition, the central second and the transition sections are folded in pleats as urged by the spiral ridges.

SUMMARY OF THE INVENTION

The present invention, in one aspect, relates to an expandable medical balloon member having torque in a first unexpanded state and a having a torque in a second unexpanded state. The torque may be released from the balloon member during an expanded state in between the first and second unexpanded state. The present invention also relates to methods of making and using the same.

The methods and balloons of the present invention can provide for improved rewrappability of the balloon members of dilatation catheter assemblies subsequent to an initial inflation thereof.

In one aspect, the present invention involves the manufacture of a balloon in such a way that a torque may be applied to the balloon member during assembly. In one embodiment, the balloon is mounted on the inner at the distal end, and a torque is applied to the inner shaft which consequently applies a torque to the balloon member resulting in a balloon member having a torque in a first unexpanded configuration. The balloon may be secured to the inner at the distal end, and the outer secured to the inner at the proximal end by tacking. When inflated, the torque which was applied to the balloon member releases, while the torque in the inner shaft remains. When deflated, i.e. during a second unexpanded state of the balloon member, the balloon member is again torqued, as if is has a "memory" of the original torque, and the torque in the inner is released. This results in better rewrap of the balloon member after an initial inflation. Of course, this is not to say that the balloon will not have better rewrap in the same fashion after more than one inflation.

Tacking of the outer to the inner after facilitates improved rewrap of the balloon member after initial inflation.

The amount of torque in the balloon member can be controlled. Suitably, a slight torque may allow the torque to more readily release when the balloon member is deflated. The amount of torque stored in the inner can act like a spring which can induce rewrapping of the balloon. The torque may be applied as a result of rotating the balloon member about the y-axis (see FIG. 6) to an angle of about 30° to about 360° from the y-axis.

The torque in the balloon member releases during inflation. The tacking of the balloon to the inner after applying a torque to the inner which results in a torque being applied to the balloon, results in a balloon which again is torqued during deflation.

In another aspect, invention also relates to a method of treating the site of a stenotic lesion in the vasculature of a patient, the method including the steps of inserting a catheter device including a balloon member and an inner shaft and an outer shaft, each having a distal end and a proximal end, the balloon member mounted on the distal end of the inner shaft and the balloon member and the inner shaft manufactured in such a way that both the inner shaft and the balloon are torqued, resulting in a balloon member having a torque, through the vasculature of a patient until it reaches the site of stenosis, and inflating the balloon member such that the torque in the balloon member is released while the torque in the inner shaft remains during the inflation of the balloon member. The inner shaft may be tacked to the outer shaft, and the balloon member may be secured to the outer shaft. After treatment, the balloon is deflated to a second unexpanded state in which it is again torqued, while the torque in the inner shaft releases. The balloon member is then removed from the vasculature. The method can also involve the step of deploying a stent, or a second balloon member at the stenotic site.

Other advantages and will become apparent from the following description.

All patents discussed herein are incorporated by reference herein in their entirety.

DETAILED DESCRIPTIONS OF THE PREFERRED EMBODIMENTS

While this invention may be embodied in many different forms, there are described in detail herein specific embodiments of the invention. This description is an exemplification of the principles of the invention and is not intended to limit the invention to the particular embodiments illustrated.

The balloon member in one embodiment, is mounted on the inner shaft of a catheter assembly and torqued during a first unexpanded state. The torque in the balloon member is reversed when the balloon member is expanded and then re-torques again in a second unexpanded state. The balloon member may be secured to the distal inner at its distal end, the inner is torqued resulting in torquing of the balloon member, and the inner then secured to the outer near the proximal end of the balloon by tacking, the balloon member also secured to the outer. The balloon may be secured to the outer in a butt joint fashion, or the outer may either be secured to the inside or to the outside of the balloon at its proximal end.

A torque is applied to the inner shaft resulting in a balloon member which has a torque in a first unexpanded state. The torque in the inner shaft remains when the balloon member is expanded. When the balloon is in a second unexpanded state, such as during removal from the vasculature of a patient, the balloon member again torques and the torque in the inner shaft releases. The balloon member re-torques during deflation. This facilitates removal from the vasculature.

Figure 1:
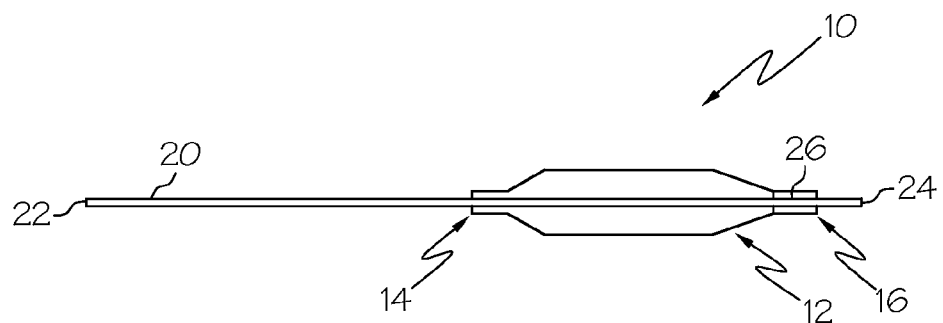
FIG. 1 is a side view of a balloon catheter showing the balloon member secured to the distal inner.

Turning now to the figures, FIG. 1 illustrates generally at 10 a catheter assembly wherein balloon 12 has a proximal end 14 and a distal end 16 and inner 20 has a proximal end 22 and a distal end 24 and balloon 12 is secured to the inner 20 at proximal end 14 of balloon and proximal end 24 of inner 20. The point of overlap, i.e. at the distal waist portion of balloon 12, wherein the balloon 12 is secured to the inner 20 is shown at 26. The balloon 12 may be secured at its distal end 16 to inner 20 using any means known in the art including, for example, welding or adhesively bonding. A tie layer may be optionally employed to enhance adhesion between balloon 12 and inner 20.

Figure 2:
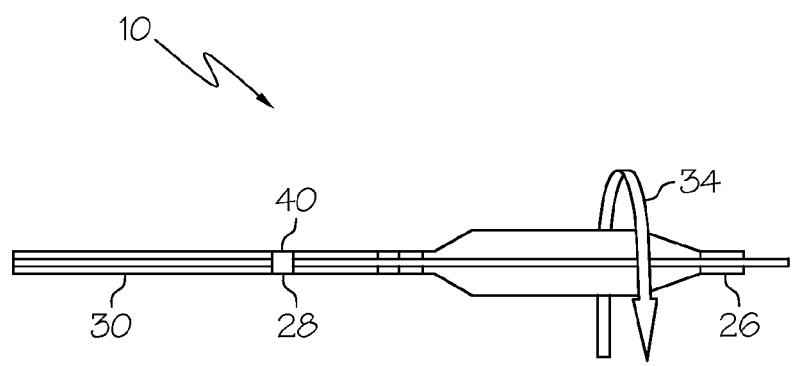
FIG. 2 is a side view of a balloon catheter illustrating torquing of the balloon member and then tacking of the outer to the inner.

FIG. 2 illustrates generally at 10 a catheter assembly according to the invention wherein the balloon 12 is secured to inner 20 at waist portion 26. The balloon has a torque, represented by the arrow 34 and the inner 20 is tacked to the distal outer 30 at distal point 40 but not around the entire circumference of the inner 20.

Figure 3:
FIG. 3 is a side view of a balloon member having a slight torque.
Figure 4:
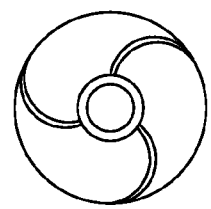
FIG. 4 is an end cross-sectional view of a balloon member with a slight torque.

FIG. 3 represents generally at 12, a balloon member to which a torque has been applied. FIG. 4 is an end view of a balloon member 12 to which a torque has been applied.

Figure 5:
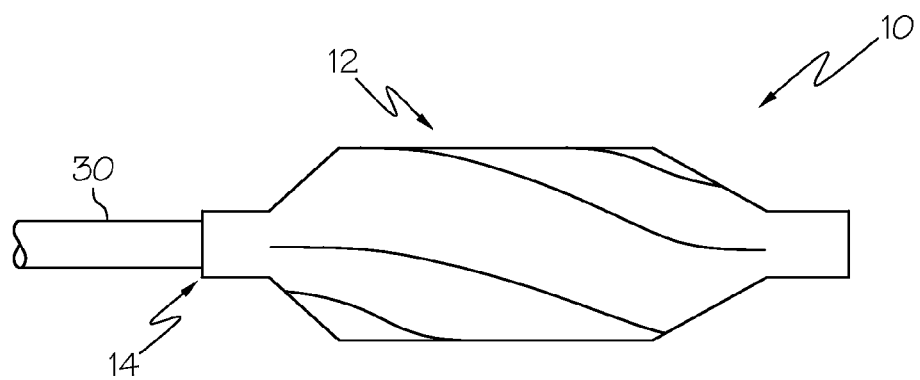
FIG. 5 is an alternative side view of a balloon member having a slight torque.
Figure 6:
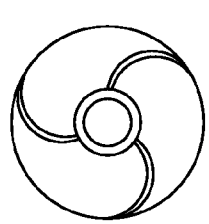
FIG. 6 is an end view of the balloon having a torque similar to that shown in FIG. 5

FIG. 5 illustrates generally at 10, a balloon catheter according to the invention showing a balloon 12 secured at its proximal end 14 at the distal outer 30. The balloon is shown with a torque. FIG. 6 is an end view of the torqued balloon 12 shown in FIG. 5.

Figure 7:
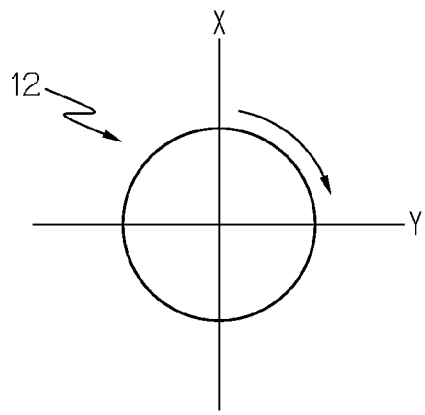
FIG. 7 shows an end view of a balloon member showing the x-axis and the y-axis intersecting the through the middle of the balloon member.

The balloons may be caused to rotate about the y-axis (shown in FIG. 6) such that they have a slight torque, or they may be more drastically torqued. The balloons may be rotated anywhere between about 15° to about 360° and more suitably between about 30° and about 360° from the y-axis, even more suitably between about 45° and 360°. An end view of balloon 12 is shown FIG. 7. Balloon 12 is shown dissected by an x- and a y-axis.

Torquing of the balloon member and then tacking the distal outer to the inner provides for better rewrap of the balloon after initial inflation. Better rewrapping leads to easier removal from the vasculature after deflation.

The balloon members according to the present invention may be formed from using any materials known to those of skill in the art. Commonly employed materials include the thermoplastic elastomeric and non-elastomeric polymers and the thermosets including the moisture curable polymers.

Examples of suitable materials include but are not limited to, polyolefins, polyesters, polyurethanes, polyamides, polyimides, polycarbonates, polyphenylene sulfides, polyphenylene oxides, polyethers, silicones, polycarbonates, styrenic polymers, copolymers thereof, and mixtures thereof. Some of these classes are available both as thermosets and as thermoplastic polymers. See commonly assigned U.S. Pat. No. 5,500,181, for example, which is incorporated by reference herein in its entirety. As used herein, the term copolymer shall be used to refer to any polymeric material formed from more than one monomer.

As used herein, the term "copolymer" shall be used to refer to any polymer formed from two or more monomers, e.g. 2, 3, 4, 5 and so on and so forth.

Useful polyamides include, but are not limited to, nylon 12, nylon 11, nylon 9, nylon 6/9 and nylon 6/6. The use of such materials is described in U.S. Pat. No. 4,906,244, for example, the entire content of which is incorporated by reference herein in its entirety.

Examples of some copolymers of such materials include the polyether-block-amides, available from Elf Atochem North America in Philadelphia, Pa. under the tradename of PEBAX®. Another suitable copolymer is a polyetheresteramide.

Suitable polyester copolymers, include, for example, polyethyelene terephthalate and polybutylene terephthalate, polyester ethers and polyester elastomer copolymers such as those available from DuPont in Wilmington, Del. under the tradename of HYTREL®.

Block copolymer elastomers such as those copolymers having styrene end blocks, and midblocks formed from butadiene, isoprene, ethylene/butylene, ethylene/propene, and so forth may be employed herein. Other styrenic block copolymers include acrylonitrile-styrene and acrylonitrile-butadiene-styrene block copolymers. Also, block copolymers wherein the particular block copolymer thermoplastic elastomers in which the block copolymer is made up of hard segments of a polyester or polyamide and soft segments of polyether.

Specific examples of polyester/polyether block copolymers are poly(butylene terephthalate)-block-poly(tetramethylene oxide) polymers such as ARNITEL® EM 740, available from DSM Engineering Plastics. and HYTREL® polymers available from DuPont de Nemours & Co, already mentioned above.

The above materials are intended for illustrative purposes only, and not as a limitation on the scope of the present invention. Suitable polymeric materials available for use are vast and too numerous to be listed herein and are known to those of ordinary skill in the art.

Suitable materials which can be employed in balloon formation are described, for example, in commonly assigned U.S. Pat. No. 6,406,457; U.S. Pat. No. 6,284,333; U.S. Pat. No. 6,171,278; U.S. Pat. No. 6,146,356; U.S. Pat. No. 5,951, 941; U.S. Pat. No. 5,830,182; U.S. Pat. No. 5,556,383; U.S. Pat. No. 5,447,497; U.S. Pat. No. 5,403,340; U.S. Pat. No. 5,348,538; and U.S. Pat. No. 5,330,428 all of which are incorporated by reference herein in their entirety.

Balloon formation may be carried out in any conventional manner using known extrusion, injection molding and other molding techniques. Typically, there are three major steps in the process which include extruding a tubular preform, molding the balloon and annealing the balloon. Depending on the balloon material employed, the preform may be axially stretched before it is blown. Techniques for balloon formation are described in U.S. Pat. No. 4,490,421, RE32,983, RE33, 561 and commonly assigned U.S. Pat. No. 5,348,538 each of which is incorporated by reference herein in its entirety.

The balloons according to the present invention may be formed into flaps or otherwise folded prior to application of the torque to the balloon member and tacking of the inner shaft to the distal outer shaft. It is common to wrap, form into flaps or otherwise fold the balloon members during the manufacturing process in order to reduce the balloon profile prior to delivery into the vasculature. For example, U.S. Pat. No. 5,350,361, incorporated by reference herein in its entirety, describes a method for preparing a tri-fold balloon configuration. Commonly assigned U.S. Pat. No. 5,147,302 and U.S. Pat. No. 5,342,307, both of which are incorporated by reference herein in their entirety, also describes a tri-fold balloon configuration and methods of shaping a balloon. Of course, other configurations may be employed as well. The configurations described herein are for illustrative purposes only, and are not intended to limit the scope of the present invention. For example, U.S. Pat. No. 6,033,380, incorporated by reference herein in its entirety, describes a six-pleated balloon configuration. The balloon may be formed into flaps or other wise folded or pleated prior to application of a torque to the balloon member.

Figure 8:
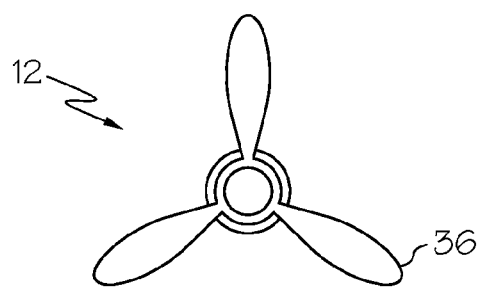
FIG. 8 shows an end view of a balloon having a tri-fold configuration.

FIG. 8 illustrates generally at 12 a balloon member having a tri-fold construction, each fold represented by the numeral 36.

The balloon may then be "heat set" in the desired fold configuration so that the balloon returns to the fold configuration when the balloon is deflated.

A balloon protector may also be applied to the distal end portion of the catheter prior to packaging and sterilization of the catheter. The sterilization process often involves exposing the catheter, with the balloon protector in place, to an elevated temperature for a predetermined time period. With certain balloon materials, such as polyolefin, the sterilization process causes the balloon to be "heat set" in the folded or wrapped condition in which it is held by the balloon protector. As a result, when the balloon protector is later removed, the balloon tends to remain in the tightly wrapped condition. One such process is described in commonly assigned U.S. Pat. No. 6,283,743 which is incorporated by reference herein in its entirety. These techniques are known to those of skill in the art.

The present invention also relates to a method of making a balloon member which may be used in combination with a catheter assembly, the catheter assembly including an inner shaft having a proximal end and a distal end. The method includes the steps of providing an inner shaft, providing a balloon member, mounting the balloon member on the inner shaft, and rotating the inner shaft such that there is a torque in both the inner and in the balloon member.

The balloon member may be secured to the inner shaft.

The method may further include the steps of forming the balloon member.

The method may further include the step of providing an outer shaft having a proximal end and a distal end. Once the inner shaft has been rotated, and a torque consequently applied to the balloon member, the inner shaft may be tacked to the proximal end of the outer shaft.

Thus, the torque may remain in the balloon member during storage prior to use. The torque reverses or releases once the balloon member is expanded to an expanded state, once the balloon has been deployed to a desired site in a patient, while the torque remains in the inner shaft. The balloon member in a second unexpanded state, such as after deflation so that the balloon member can be removed from the patient, again torques while the torque in the inner shaft releases. This rewrap of the balloon member facilitates removal of the balloon member from the vasculature of the patient.

The balloon member may be in its first unexpanded state during deployment to the site of a stenosis in the vasculature of a patient, is then inflated with inflation fluid resulting in release or reversal of the torque from the balloon member, and is then deflated to a second unexpanded state resulting again in a torque in the balloon member. The method results in a balloon member that has better rewrap.

The balloon member may also be used in combination with other medical devices such as a stent, or with another balloon member, for example.

The present invention also relates to a method of decreasing the stenosis in the vasculature of a patient, the method including the steps of inserting a catheter device including a balloon member and an inner shaft and an outer shaft, each having a distal end and a proximal end, the balloon member mounted on the inner shaft and the balloon member and the inner shaft in a torqued configuration, through the vasculature of a patient until it reaches the site of stenosis, and inflating the balloon member such that the torque in the balloon member releases while the torque in the inner shaft remains. After treatment, the balloon is deflated to a second unexpanded state in which the torque is again present, while the torque in the inner shaft releases. The balloon member is then removed from the vasculature. The method can also involve the step of deploying a stent, or a second balloon member at the stenotic site.

The above disclosure is intended to be illustrative and not exhaustive. The description will suggest many variations and alternatives to those of ordinary skill in the art. All of these alternatives and variations are intended to be included within the scope of the attached claims. Those familiar with the art may recognize other equivalents to the specific embodiments described herein which equivalents are also intended to be encompassed by the claims attached hereto.

The invention claimed is:

1. An expandable medical balloon having a first unexpanded state, an expanded state and a second unexpanded state, said balloon being mounted on an inner shaft of a catheter assembly, said inner shaft having a torque in the first unexpanded state of said balloon, said balloon having a torque in the first unexpanded state and having a torque in the second unexpanded state, said inner shaft being tacked to an outer shaft, wherein the torque in the inner shaft remains and the torque in the balloon is released when the balloon is expanded and the torque in the inner shaft releases when said balloon is in the second unexpanded state.

2. The medical balloon of claim 1 said inner shaft having a proximal end and a distal end, said balloon is being secured to said inner shaft at said distal end of said inner shaft.

3. The medical balloon of claim 2, said catheter assembly comprising an outer shaft having a proximal end and a distal end.

4. The medical balloon of claim 3, wherein said inner shaft is tacked to said outer shaft at said proximal end of said outer shaft.

5. The medical balloon of claim 1, further used in combination with a stent.

6. The medical balloon of claim 1, wherein said medical balloon is rotated about the y-axis at an angle of about 30° from the y-axis or less in said first unexpanded state.

7. The medical balloon of claim 1, wherein said medical balloon is rotated about the y-axis at an angle of about 30° to about 90° from the y-axis in said first unexpanded state.

8. The medical balloon of claim 1, wherein said medical balloon is rotated at an angle of about 30° to about 360° from the y-axis in said first unexpanded state.

9. The medical balloon of claim 1, said medical balloon comprising at least one member selected from the group consisting of thermoplastic polymers, thermosetting polymers or mixtures thereof.

10. The medical balloon of claim 1, said medical balloon comprising at least one material selected from the group consisting of elastomeric polymers, non-elastomeric polymers and mixtures thereof.

11. The medical balloon of claim 1, said medical balloon comprising at least one member comprises at least one material which is a thermoplastic block copolymer.

12. The medical balloon of claim 1, said medical balloon comprising at least one polymer selected from the group consisting of polyolefins, polyesters, polyethers, polyamides, polyimides, polyphenylene sulfides, polyphenylene oxides, polyurethanes, polycarbonates, silicones, styrenic polymers, copolymers thereof, and mixtures thereof.

13. The medical balloon of claim 1, wherein said medical balloon is in a folded configuration.

14. The medical balloon of claim 13, wherein said medical balloon is in a folded configuration having two or more wings.

15. The medical balloon of claim 1, wherein said medical balloon is in a folded configuration having three or more wings.

16. A balloon catheter having an expandable member formed according to a method comprising the steps of:
    a) providing an inner shaft having a distal end and a proximal end;
    b) providing a balloon member having a distal end and a proximal end, said balloon member having a first unexpanded state, an expanded state and a second unexpanded state;
    c) mounting said balloon member on said inner shaft; and
    d) providing an outer shaft;
    e) applying a torque to said inner shaft resulting in application of a torque to said balloon member, said torque being applied so that said inner shaft has a torque when said balloon member is in the first unexpanded state, the balloon also having a torque in the first unexpanded state; and
    f) tacking the inner shaft to the outer shaft such that the torque remains in the inner shaft when said balloon member is expanded but releases in the inner shaft when said balloon is in its second unexpanded state, said balloon again has torque in said second unexpanded state.

17. The balloon catheter formed according to the method of claim 16, the method further comprising the step of forming said balloon member.

18. The balloon catheter formed according to the method of claim 16, the method further comprising the step of securing the balloon at its distal end to the distal end of the inner shaft.

19. The balloon catheter formed according to the method of claim 18, the method further comprising the step of tacking the distal outer shaft to the inner shaft.

20. The balloon catheter formed according to the method of claim 16, the method further comprising the step of folding the balloon prior to applying said torque.

21. The balloon catheter formed according to the method of claim 20 wherein after folding, said balloon member has 3 or more wings.

22. A method of providing an expandable member of a balloon catheter with improved rewrap, the method comprising the steps of:
    a) providing an inner shaft having a distal end and a proximal end;
    b) providing a balloon member having a distal end and a proximal end and a first unexpanded state, an expanded state and a second unexpanded state;
    c) mounting said balloon member on said inner shaft;
    d) providing an outer shaft;
    e) applying a torque to said inner shaft resulting in application of a torque to said balloon member, said torque being applied so that said inner shaft has a torque when said balloon member is in the first unexpanded state, said balloon member also having a torque in said first unexpanded state; and
    f) tacking the inner shaft to the outer shaft such that the torque remains in the inner shaft when the balloon is expanded and releases when said balloon is in its second unexpanded state, the torque in the balloon releasing when the balloon is expanded and the balloon again having a torque in said second unexpanded state.

23. The method of claim 22 further comprising the step of forming said balloon member.

24. The method of claim 22 further comprising the step of securing the balloon at its distal end to the distal inner shaft.

25. The method of claim 22 further comprising the step of tacking the distal outer shaft to the inner shaft near the proximal end of said balloon.

26. The method of claim 22 further comprising the step of folding the balloon member prior to application of said torque.

27. The method of claim 26 wherein after folding, said balloon member has 2 or more wings.

28. The method of claim 26 wherein after folding, said balloon member has 3 or more wings.

29. The method of claim 22 wherein said balloon member is rotated about the y-axis at an angle of about 30° to about 360° from the y-axis in said first unexpanded state.

30. The method of claim 22 wherein said balloon member is rotated about the y-axis at an angle of about 30° to about 90° from the y-axis in said first unexpanded state.

31. The method of claim 22 wherein said balloon member is rotated about the y-axis at an angle of about 45° from the y-axis in said first unexpanded state.

32. The method of claim 22 wherein said balloon member comprises at least one member selected from the group consisting of thermoplastic block copolymers.

33. The method of claim 22 wherein said balloon member comprises at least one member selected from the group consisting of polyolefins, polyesters, polyethers, polyimides, polyamides, polyphenylene sulfides, polyphenylene oxides, polycarbonates, silicones, styrenic polymers, copolymers thereof and mixtures thereof.

34. The method of claim 22 further comprising the step of disposing a stent about the balloon member.

* * * * *

UNITED STATES PATENT AND TRADEMARK OFFICE
CERTIFICATE OF CORRECTION

| | | |
|---|---|---|
| PATENT NO. | : 7,597,702 B2 | Page 1 of 1 |
| APPLICATION NO. | : 10/663641 | |
| DATED | : October 6, 2009 | |
| INVENTOR(S) | : Eidenschink et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1553 days.

Signed and Sealed this

Twenty-eighth Day of December, 2010

David J. Kappos
*Director of the United States Patent and Trademark Office*